United States Patent
Gong et al.

(10) Patent No.: US 8,778,893 B2
(45) Date of Patent: Jul. 15, 2014

(54) (R)-1-(4-(4-FLUORO-2-METHYL-1H-INDOL-5-YLOXY)-5-METHYLPYRROLO[2,1-F][1,2,4]TRIAZIN-6-YLOXY)PROPAN-2-OL METABOLITES

(75) Inventors: Jiachang Gong, Belle Mead, NJ (US); Lisa J. Christopher, East Windsor, NJ (US); Vinod Kumar Arora, Cheshire, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 155 days.

(21) Appl. No.: 13/500,365

(22) PCT Filed: Oct. 4, 2010

(86) PCT No.: PCT/US2010/051274
§ 371 (c)(1),
(2), (4) Date: Apr. 5, 2012

(87) PCT Pub. No.: WO2011/044019
PCT Pub. Date: Apr. 14, 2011

(65) Prior Publication Data
US 2012/0196814 A1 Aug. 2, 2012

Related U.S. Application Data

(60) Provisional application No. 61/248,581, filed on Oct. 5, 2009.

(51) Int. Cl.
*C07H 15/26* (2006.01)
*C07D 487/04* (2006.01)

(52) U.S. Cl.
USPC ............. 514/25; 514/243; 536/17.4; 544/183

(58) Field of Classification Search
CPC .............................. C07H 15/26; C07D 487/04
USPC ...................... 514/25, 243; 536/17.4; 544/183
See application file for complete search history.

(56) References Cited

U.S. PATENT DOCUMENTS

| | | | |
|---|---|---|---|
| 6,869,952 B2 * | 3/2005 | Bhide et al. ................... | 514/243 |
| 7,265,113 B2 | 9/2007 | Bhide et al. | |
| 7,521,450 B2 | 4/2009 | Bhide et al. | |
| 7,820,814 B2 | 10/2010 | Bhide et al. | |

FOREIGN PATENT DOCUMENTS

| | | |
|---|---|---|
| WO | WO 03/080064 | 10/2003 |
| WO | WO 2004/009784 | 1/2004 |

OTHER PUBLICATIONS

Wolff, Manfred E. "Burger's Medicinal Chemistry, 5ed, Part I", John Wiley & Sons, 1995, pp. 975-977.*
Banker, G.S. et al, "Modern Pharmaceutics, 3ed.", Marcel Dekker, New York, 1996, p. 596.*
Fura, A. et al.; Journal of Medicinal Chemistry, vol. 47, No. 18, pp. 4339-4351 (2004).

* cited by examiner

*Primary Examiner* — Traviss C McIntosh, III
(74) *Attorney, Agent, or Firm* — Elliott Korsen

(57) ABSTRACT

The present invention is directed to metabolites of (R)-1-(4-(4-fluoro-2-methyl-1H-indol-5-yloxy)-5-methylpyrrolo[2,1-f][1,2,4]triazin-6-yloxy)propan-2-ol, the compound of formula (I), pharmaceutical compositions thereof, and to methods of using the metabolites and the pharmaceutical compositions in the treatment of cancer.

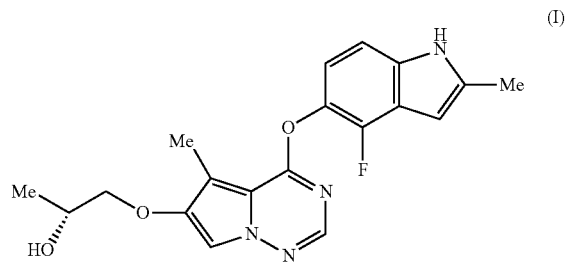

12 Claims, No Drawings

(R)-1-(4-(4-FLUORO-2-METHYL-1H-INDOL-5-YLOXY)-5-METHYLPYRROLO[2,1-F][1,2,4]TRIAZIN-6-YLOXY)PROPAN-2-OL METABOLITES

FIELD OF THE INVENTION

The invention relates to metabolites of (R)-1-(4-(4-fluoro-2-methyl-1H-indol-5-yloxy)-5-methylpyrrolo[2,1-f][1,2,4]triazin-6-yloxy)propan-2-ol, pharmaceutical compositions thereof, and to methods of using the metabolites and the pharmaceutical compositions in the treatment of cancer.

BACKGROUND OF THE INVENTION

The compound of formula (I)

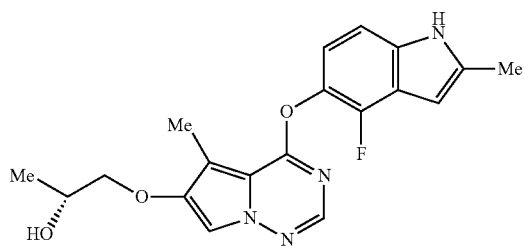 [SMILES: Cc1cc2c(F)c(Oc3ncnn4cc(OC[C@@H](C)O)c(C)c34)ccc2[nH]1]

(R)-1-(4-(4-fluoro-2-methyl-1H-indol-5-yloxy)-5-methylpyrrolo[2,1-f][1,2,4]triazin-6-yloxy)propan-2-ol, is a protein tyrosine kinase inhibitor, a VEGFR-2 and FGFR inhibitor and is useful in the treatment of cancer.

The L-alanine ester prodrug of Compound I (Compound Ia)

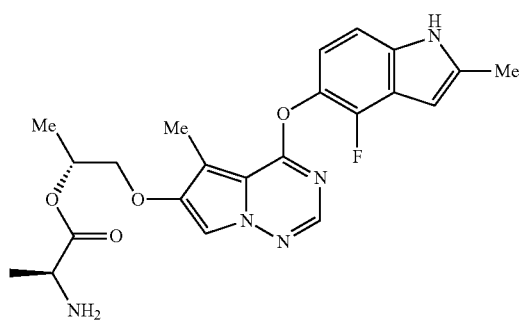

is currently in clinical development as an agent for the treatment of cancer.

The compounds of formula (I) and (Ia) and their preparation have been previously described in U.S. Pat. No. 6,869,952, issued Mar. 22, 2005, U.S. Pat. No. 7,265,113, issued Sep. 4, 2007, U.S. Pat. No. 7,521,450, issued Apr. 21, 2009 and U.S. Pat. No. 7,671,199, issued Mar. 2, 2010.

SUMMARY OF THE INVENTION

The present invention is directed to compounds which are metabolites of the compound of formula (I), pharmaceutical compositions thereof and to methods of treating cancer.

DETAILED DESCRIPTION OF EMBODIMENTS OF THE INVENTION

The present invention is directed to compounds which are metabolites of the compound of formula (I)

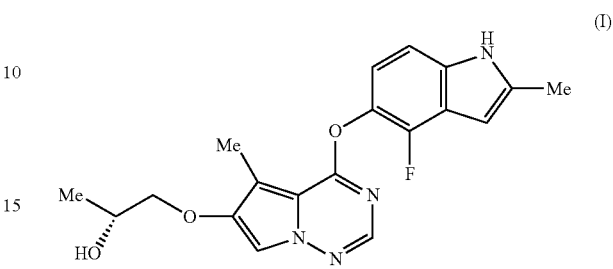

or pharmaceutically acceptable salt forms thereof.

In another embodiment of the invention, the compounds which are metabolites of the compound of formula (I) are present in substantially pure form.

The substantially pure compounds may be combined with other ingredients to form pharmaceutical compositions thereof.

The compounds which are metabolites of the compound of formula (I) are represented by the compounds of formula (II), (III) and (IV).

In another embodiment, the invention is directed to a purified compound of formula (II),

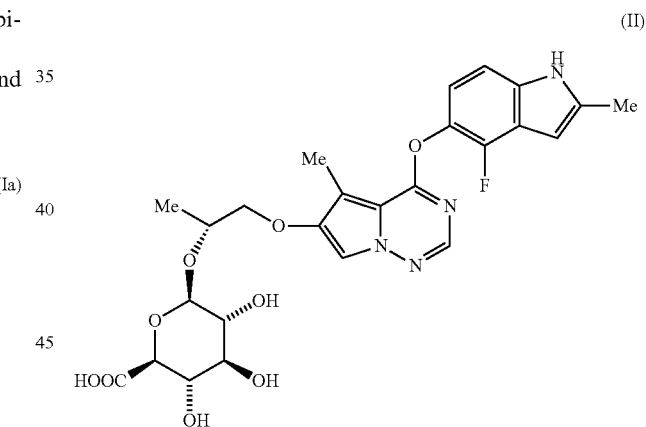

or pharmaceutically acceptable salt forms thereof.

In another embodiment, the invention is directed to a purified compound of formula (III),

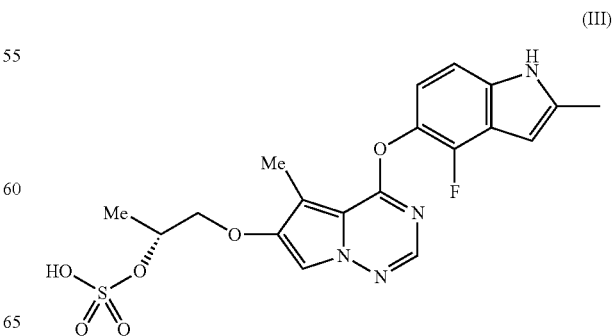

or pharmaceutically acceptable salt forms thereof.

In another embodiment, the invention is directed to a purified compound of formula (IV),

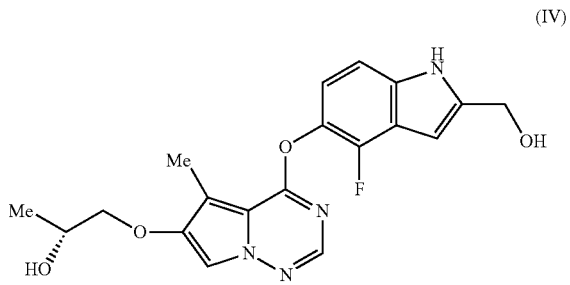 [SMILES: Cc1c(OC[C@@H](C)O)cn2ncnc(Oc3ccc4[nH]c(CO)cc4c3F)c12]

(IV)

or pharmaceutically acceptable salt forms thereof.

In another embodiment, the invention is directed to a purified compound which is a metabolite of the compound of formula (I), wherein the metabolite is a compound having a molecular ion [M+H]$^+$ of m/z 547 and a major MS/MS fragment at m/z 371.

In another embodiment, the invention is directed to a purified compound which is a metabolite of the compound of formula (I), wherein the metabolite is a compound having a molecular ion [M+H]$^+$ of m/z 451, and major MS/MS fragments at m/z 371 and 353, and the MS$^3$ fragmentation of m/z 371 having fragments of 353, 313 and 148.

In another embodiment, the invention is directed to a purified compound which is a metabolite of the compound of formula (I), wherein the metabolite is a compound having [M+H]$^+$ of m/z 387 and major MS/MS fragments at m/z 369, 329 and 311.

In another embodiment, there is provided a pharmaceutical composition, comprising a pharmaceutically acceptable carrier and a therapeutically effective amount of a compound of the present invention.

In another embodiment, there is provided a method for treating cancer, comprising administering to a patient in need thereof a therapeutically effective amount of a compound of the present invention.

In another embodiment, there is provided the use of the compounds of the present invention in therapy.

In another embodiment, there is provided the use of the compounds of the present invention in the preparation of a medicament for the treatment of cancer.

The invention may be embodied in other specific forms without departing from the spirit or essential attributes thereof. This invention also encompasses all combinations of preferred aspects and examples of the invention noted herein. It is understood that any and all embodiments of the present invention may be taken in conjunction with any other embodiment to describe additional even more preferred embodiments of the present invention. Furthermore, any elements of an embodiment are meant to be combined with any and all other elements from any of the embodiments to describe additional embodiments.

DEFINITIONS

The compound which is a metabolite of the compound of formula I form salts which are also within the scope of this invention. Reference to a compound herein is understood to include reference to salts thereof, unless otherwise indicated. The term "salt(s)", as employed herein, denotes acidic and/or basic salts formed with inorganic and/or organic acids and bases. In addition, when a compound of formula I contains both a basic moiety, such as, but not limited to an amine or a pyridine ring, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful, e.g., in isolation or purification steps which may be employed during preparation. Salts of the compounds may be formed, for example, by reacting a compound with an amount of acid or base, such as an equivalent amount, in a medium such as one in which the salt precipitates or in an aqueous medium followed by lyophilization.

Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides (formed with hydrochloric acid), hydrobromides (formed with hydrogen bromide), hydroiodides, 2-hydroxyethanesulfonates, lactates, maleates (formed with maleic acid), methanesulfonates (formed with methanesulfonic acid), 2-naphthalenesulfonates, nicotinates, nitrates, oxalates, pectinates, persulfates, 3-phenylpropionates, phosphates, picrates, pivalates, propionates, salicylates, succinates, sulfates (such as those formed with sulfuric acid), sulfonates, tartrates, thiocyanates, toluenesulfonates such as tosylates, undecanoates, and the like.

Exemplary basic salts include ammonium salts, alkali metal salts such as sodium, lithium, and potassium salts, alkaline earth metal salts such as calcium and magnesium salts, salts with organic bases (for example, organic amines) such as benzathines, dicyclohexylamines, hydrabamines [formed with N,N-bis(dehydroabietyl)ethylenediamine], N-methyl-D-glucamines, N-methyl-D-glucamides, t-butyl amines, and salts with amino acids such as arginine, lysine and the like. Basic nitrogen-containing groups may be quaternized with agents such as lower alkyl halides (e.g., methyl, ethyl, propyl, and butyl chlorides, bromides and iodides), dialkyl sulfates (e.g., dimethyl, diethyl, dibutyl, and diamyl sulfates), long chain halides (e.g., decyl, lauryl, myristyl and stearyl chlorides, bromides and iodides), aralkyl halides (e.g., benzyl and phenethyl bromides), and others.

Metabolites of the compound of formula I, and salts thereof, may exist in their tautomeric form, in which hydrogen atoms are transposed to other parts of the molecules and the chemical bonds between the atoms of the molecules are consequently rearranged. It should be understood that all tautomeric forms, insofar as they may exist, are included within the invention. Additionally, inventive compounds may have trans and cis isomers and may contain one or more chiral centers, therefore existing in enantiomeric and diastereomeric forms. The invention includes all such isomers, as well as mixtures of cis and trans isomers, mixtures of diastereomers and racemic mixtures of enantiomers (optical isomers). When no specific mention is made of the configuration (cis, trans or R or S) of a compound (or of an asymmetric carbon), then any one of the isomers or a mixture of more than one isomer is intended. The processes for preparation can use racemates, enantiomers, or diastereomers as starting materials. When enantiomeric or diastereomeric products are prepared, they can be separated by conventional methods, for example, by chromatographic or fractional crystallization. The inventive compounds may be in the free or hydrate form.

The present invention is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed.

In addition, metabolites of the compound of formula I may have prodrug forms. Any compound that will be converted in vivo to provide the bioactive agent (i.e., a compound of formula I) is a prodrug within the scope and spirit of the invention.

For example, prodrug compounds of metabolites of formula I may be carboxylate ester moieties. A carboxylate ester may be conveniently formed by esterifying any of the carboxylic acid functionalities found on the disclosed ring structure(s). Various forms of prodrugs are well known in the art.

It should further be understood that solvates (e.g., hydrates) of the compounds of formula I are also within the scope of the present invention.

"Stable compound" and "stable structure" are meant to indicate a compound that is sufficiently robust to survive isolation to a useful degree of purity from a reaction mixture, and formulation into an efficacious therapeutic agent. The present invention is intended to embody stable compounds.

"Substantially pure" as used herein is intended to include a compound having a purity greater than 90 weight percent, including 90, 91, 92, 93, 94, 95, 96, 97, 98, 99, and 100 percent.

As one example, a metabolite of the compound of the formula (I) can be substantially pure in having a purity greater than 90 percent (by weight), where the remaining less than 10 percent of material comprises other metabolite(s) of the compound of the formula (I), the compound of formula (I), and/or reaction and/or processing impurities arising from its preparation.

A metabolite of the compound of the formula (I) in substantially pure form may be employed in pharmaceutical compositions to which other desired components are added, for example, excipients, carriers, or active chemical entities of different molecular structure.

"Therapeutically effective amount" is intended to include an amount of a compound of the present invention alone or an amount of the combination of compounds claimed or an amount of a compound of the present invention in combination with other active ingredients effective to inhibit protein tyrosine kinase activity, such as but not limited to VEGF kinase activity, or effective to treat or prevent cancer.

As used herein, "treating" or "treatment" cover the treatment of a disease-state in a mammal, particularly in a human, and include: (a) preventing the disease-state from occurring in a mammal, in particular, when such mammal is predisposed to the disease-state but has not yet been diagnosed as having it; (b) inhibiting the disease-state, i.e., arresting it development; and/or (c) relieving the disease-state, i.e., causing regression of the disease state.

Metabolite Isolation

The metabolites of the compound of formula (I) were identified from in vitro incubations with liver microsomes, liver S9 fraction and hepatocytes, using either cold or C-14 labeled compound of formula (Ia). They were identified based on HPLC retention times, MS and MS/MS fragmentations, and NMR analysis.

Liver Microsomes

The compound of formula (Ia) was incubated with pooled liver microsomes from mouse, rat, dog, monkey and human. Incubations were carried at 37° C. in a shaking water bath. The incubation mixtures consisted of: 0.1 M potassium phosphate buffer (pH 7.4), 0.5 mM NADPH, 0.5 mg/mL liver microsomal protein, and 20 µM of compound of formula Ia. After a 5 minute pre-incubation at 37° C., the incubations were initiated with the addition of compound of formula Ia and NADPH. After 60 min, the mixtures were quenched by adding 1 volume of cold acetonitrile. The samples were vortex mixed and centrifuged for 10 min at 14000 rpm. Aliquots of supernatant (200 µL) were taken for LC/MS/MS analysis.

Liver S9 Fractions

The compound of formula Ia was incubated with pooled liver S9 fractions from human at 37° C. in a shaking water bath. The incubation mixtures consisted of: 0.1 M potassium phosphate buffer (pH 7.4), 0.5 mM PAPS, 0.5 mg/mL liver S9 protein, and 20 µM of compound of formula (Ia). The mixture was allowed to incubate for 2 h and was quenched by the addition of cold acetonitrile. The samples were vortex mixed and centrifuged for 10 min at 14000 rpm. Aliquots of supernatant (200 µL) were taken for LC/MS/MS analysis.

Hepatocytes

The compound of formula (Ia) was incubated with hepatocytes from mouse, rat, dog, monkey and human at concentrations of 3 and 30 µM. The incubation mixtures were prepared by adding 4.5 µL/mL of the 0.67 and 6.7 mM C-14 labeled stock solutions in acetonitrile, for 3 and 30 µM incubations, respectively, to an appropriate amount of incubation medium (2 to 5 mL) containing $10^6$ cells/mL. All samples were incubated at 37° C. for 3 h in a NAPCO $CO_2$ 6000 incubator maintained under a 5% $CO_2$ atmosphere. The vials were shaken gently on an orbital shaker (VWR Scientific Products) at 90 rpm. The incubations were quenched by adding 1 volume of acetonitrile. Hepatocyte suspensions that had been quenched with acetonitrile were centrifuged at 14,200 g for 10 min. Radioactivity in the supernatants was measured by liquid scintillation counting (20 µL aliquot). Additional aliquots of the supernatants (20 µL) were injected onto the HPLC for metabolite profiling.

The metabolites of the compound of formula (I) were also identified from urine, bile, feces and plasma samples from animals and humans after administration of C-14 labeled compound of formula (Ia). A representative study is described below.

Bile-Duct Cannulated Rats

Bile-Duct Cannulated Male Sprague-Dawley rats (n=3) were dosed orally with C-14 labeled compound of formula (Ia) at a target dose of 100 mg/kg, 100 µCi/kg. The dosing solution was prepared in 50 mM citrate buffer the night before dosing and stored at room temperature in the dark. Bile, urine and feces for metabolite identification were obtained over intervals through 48 h post dose. Blood samples were collected from each rat before dosing and 1, 2, 4, 6, 12, 24 and 48 h after dosing. Plasma was prepared from the blood samples by centrifuging for 15 min at 1000 g.

Bile

A representative pooled bile sample was prepared by combining a 5% portion of the volume from each individual bile sample/each animal excreted over the 0-48 hour interval. The pooled rat bile was diluted 1:1 (vol/vol) by addition of water to bile. The diluted mixture was centrifuged on an Eppendorf 5417C centrifuge (Brinkmann Instruments, Westbury, N.Y.)

at 14,000 g for 10 min. An aliquot of the supernatant (20 μl) was injected onto LC/MS/MS for metabolite identification.

Urine

A representative pooled urine sample was prepared by combining a 20% portion of the volume from each individual urine sample/each animal excreted over the 0-48 hour interval. The pooled rat urine was centrifuged at 14,200 g for 10 min. An aliquot of the supernatant (30 nl) was injected onto LC/MS/MS for metabolite identification.

Plasma

Two pooled plasma samples (1 h and 4 h) were prepared by combining equal volumes of the individual plasma samples that were collected at each time point. The pooled plasma samples were each extracted once with 5 mL of acetonitrile/methanol (50:50 vol/vol) and an additional two times with 3 mL of acetonitrile/methanol. After the addition of organic solvent in each extraction step, samples were vortexed to re-suspend the solid material and then sonicated for 5 min. The extracted samples were centrifuged at 4,000 rpm for 10 min at 5° C. in an IEC Centra-7R refrigerated centrifuge, and the supernatants from each centrifugation step were combined. The combined supernatants were evaporated to dryness at room temperature under a stream of nitrogen gas. The dried residues were reconstituted in 350 μL of mobile phase in 80%/20% (vol/vol) water containing acetonitrile. The extracted plasma samples were then centrifuged at 14,000 rpm for 10 min at 5° C. in a Heraeus Biofuge Fresco centrifuge. The supernatants were then transferred to autosampler vials and a 100 μL aliquot was injected onto LC/MS/MS for metabolite identification.

Feces

A representative pooled fecal sample was prepared by combining a 5% of each individual fecal homogenate/each animal excreted over the 0-48 hour interval for 3 animals. Pooled fecal homogenate samples (1 mL) were extracted with 2 mL of methanol/acetonitrile (50:50 v/v). The mixtures were vortex mixed, sonicated for 5 min and centrifuged at 4000 g for 15 min. The supernatants were collected into a new tube, and the remaining pellet was extracted twice with 2 mL of methanol/acetonitrile/water (1:1:1 v/v/v). The combined supernatants were evaporated to dryness under nitrogen. The residue was suspended in 0.50 mL of methanol/water (1:1) and centrifuged at 14000 g for 10 min. The supernatants were then transferred to autosampler vials and a 60 μL aliquot was injected onto LC/MS/MS for metabolite identification.

HPLC Analysis

HPLC was performed on a Shimadzu Class VP® system equipped with two pumps (model LC-10AT), an autoinjector (SIL-10AD) and a photodiode array detector (SPD-M10A). A Zorbax® SB C-18 column (2.1 mm×150 mm, 5 micron) equipped with a guard column was used for biotransformation profiling. The column eluent was monitored at a wavelength of 240 nm. A gradient of two mobile phases, A and B, was used for HPLC profiling. Solvent A consisted of water containing 0.1% trifluoroacetic acid. Solvent B consisted of acetonitrile. Solvent B was increased linearly between time intervals: 10% (0 min) 25% (8 min), 30% (20 min), 30% (32 min), 42% (38 min), 49% (50 min), 88% (60 min) and 90% (65 min). The mobile phase flow rate was 0.3 mL/min. Drug-related peaks were identified by comparison of retention times with synthetic reference standards and by their UV spectra with the Shimadzu diode-array detector.

For quantification of radioactivity, HPLC eluent was collected in 15-sec intervals on 96-well Packard Lumaplates® with a Gilson Model FC 204 fraction collector (Gilson, Middleton, Wis.). Each fraction of column eluent was evaporated to dryness on a Savant Speed-Vac (Savant Instruments Inc., Holbrook, N.Y.) and counted for radioactivity with a Packard Top Count® microplate scintillation analyzer (Packard Biosciences, Downers Grove, Ill.).

Identification of Metabolites by LC/MS and LC/MS/MS Analysis

The LC/MS/MS system consisted of a Finnigan LTQ ion-trap mass spectrometer (Thermo Finnigan, San Jose, Calif.) interfaced with a Shimadzu Class VP HPLC system. The ESI source was set in positive ion mode as follows: voltage, 4 kV; current, 10 μA; and capillary temperature, 275° C. MS data were collected for a mass range of 100-1000 amu, and MS/MS data were acquired with the following parameters: isolation width, 1.5 amu; collision energy, 35 ev; and activation time, 30 ms. The nitrogen flow rate, spray current and voltages were adjusted to give maximum sensitivity for compound. LC/MS/MS analyses were performed to identify the drug related compounds.

Synthetic Preparation

Compounds III and IV were also prepared synthetically as described in the schemes shown below.

Step 1:

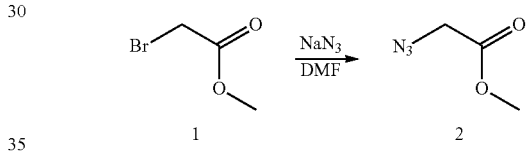

Methyl bromoacetate (1) (5.0 g, 0.0326 moles) and sodium azide (2.33 g, 0.0359 moles) were dissolved in DMF and stirred at RT for 16 hrs. A white solid appeared in the reaction and the reaction mass was diluted with water and extracted into diethyl ether (100 ml×3). The combined organic layers were washed with water (100 ml) and brine (50 ml), dried over anhyd. $Na_2SO_4$ and concentrated under vacuum to give 3.0 g of a colorless liquid (79.8%). $H^1$-NMR (400 MHz, $CDCl_3$) δ ppm: 3.83 (s, 3H), 3.91 (s, 2H), GCMS-m/z=115. IR ($cm^{-1}$): 1202, 1356, 1438, 1673, 1743, 2101, 2201, 2393, 2957.

Step 2:

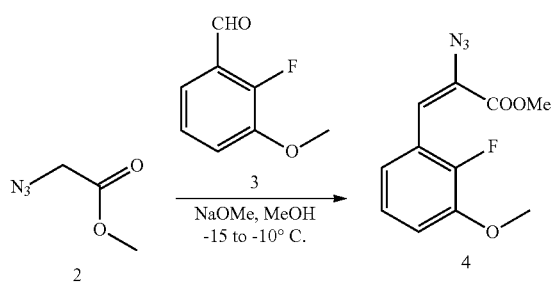

In a dry RB flask, methanol (dry) (20 ml) was charged under nitrogen atmosphere, and sodium metal (595 mg, 0.0259 moles) was added and stirred until the metal was dissolved. The reaction mixture was cooled to −15° C. To this, a mixture of aldehyde 3 (10.0 g, 0.06475 moles) and azide 2

(0.2590 moles) in methanol (25 ml) were added slowly, and stirred an additional 3 hr at −10° C. After completion, the reaction mixture was quenched with ice cold water and stirred for 10 min. A yellow solid was separated and filtered on a Buchner funnel, washed with water and dried under vacuum to yield 5.8 g (36%). H$^1$-NMR (400 MHz, CDCl$_3$) δ ppm: 3.92 (s, 3H), 3.95 (s, 3H), 6.96-7.00 (m, 1H), 7.10-7.12 (m, 1H), 7.14 (s, 1H), 7.84 (q, J=2.8, 6.4 Hz, 1H); LCMS: [Zorbax SB C18 (4.6×50) mm, 5 µm, positive mode. Mobile phase-A: 10% methanol-90% water-0.1% TFA; Mobile phase-B: 90% Methanol-10% water-0.1% TFA. Flow rate: 5 mL/min]: 99.3% (m/z=224, after N$_2$ elimination).

Step 3:

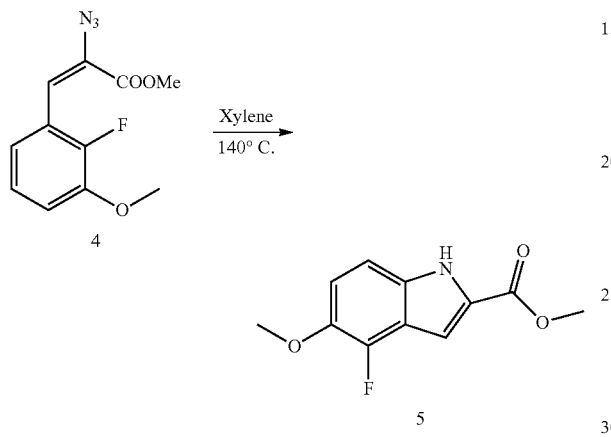

Compound 4 (3.0 g, mmol) was taken into xylene (150 ml) under nitrogen atmosphere and heated to reflux for 30 min, The reaction was monitored by TLC and upon completion, the xylene was evaporated and the obtained residue was purified by silica gel column chromatography to give 0.4 g of a yellow solid (15%). H$^1$ NMR (400 MHz, CDCl$_3$) δ ppm: 3.96 (s, 3H), 3.97 (s, 3H), 7.13 (q, J=0.8, 2.0 Hz, 2H), 7.28 (d, J=2.0 Hz, 1H), 8.87 (bs, 1H) LCMS: [Purosphoer@ star rp-18 (4.6×30) mm, 3 µm. Mobile phase-A: 20 mm of ammonium acetate-90% of water-10% acetonitrile. Mobile phase-B: 20 mm of ammonium acetate in 10% of water-90% of acetonitrile. Flow rate: 2.5 ml/min]: 98% (m/z=222). HPLC purity: [X bridge phenyl (4.6×150 mm) 3.5 µm SC/749, Buffer: 0.05% TFA in water and pH=2.5, Mobile phase-A: Buffer:Acetonitrile (95:5), Mobile phase B: Acetonitrile:Buffer (95:5). Flow rate: 1 ml/min]: Purity 98%.

Step 4:

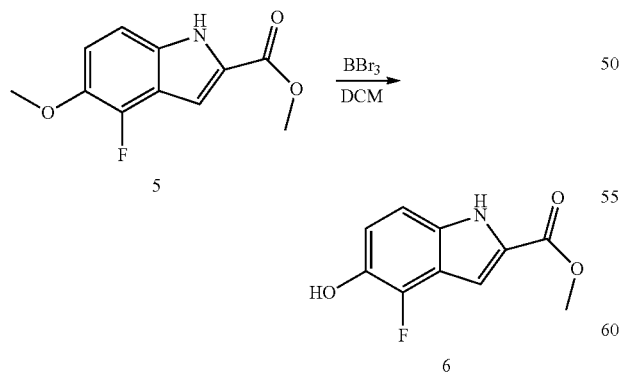

Indole compound 5 (0.2 g, 0.896 mmol) was dissolved in DCM under nitrogen atmosphere and cooled to 0° C. BBr$_3$ (1M solution in DCM) (8.96 mmol) was added and the reaction mixture was stirred at RT for 16 hr. After completion of the reaction, it was quenched with methanol at 0° C. The reaction mixture was concentrated under reduced pressure. The residue obtained was dissolved in ethyl acetate and washed with water and brine, dried over anhyd. Na$_2$SO$_4$, and concentrated to give 0.140 g of a brown solid (75%). H$^1$-NMR (400 MHz, CDCl$_3$) δ ppm: 3.95 (s, 3H), 4.88 (bs, 1H), 7.03-7.10 (m, 2H), 7.21 (s, 1H), 8.85 (bs, 1H). LCMS: [Purosphoer@ star rp-18 (4.6×30) mm, 3 µm. Mobile phase-A: 20 mm of ammonium acetate-90% of water-10% acetonitrile. Mobile phase-B: 20 mm of ammonium acetate in 10% of water-90% of acetonitrile. Flow rate: 2.5 ml/min]: 97.04% (m/z=208.2). HPLC: [Sunfire C18, (150×4.6 mm) 3.5 µm, SC/862, Buffer: 0.5% TFA, in water pH adjusted to 2.5 using dil. Ammonia. Mobile phase-A: Buffer:acetonitrile (95:5), Mobile phase-B: acetonitrile:Buffer (95:5), Flow rate: 1 mL/min] Purity: 96.08%

Step 5:

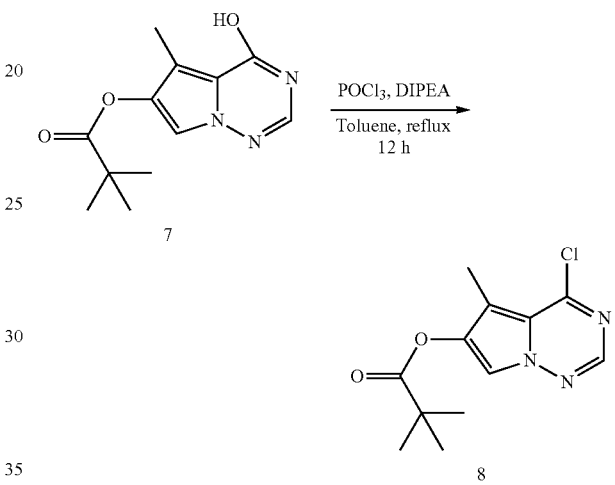

To a mixture of pyrrolotriazine 7 (2.0 g, 8.0 mmol) and toluene (20 ml) was added DIPEA (1.55 g 12 mmol). After stirring for 15 min., POCl$_3$ (1.8 g 12 mmol) was added at room temperature, heated to 110° C. and maintained for 12 hr. After completion of the reaction, it was quenched with ice cold water and extracted into ethyl acetate. The combined organic layer was washed with brine, water, dried over Na$_2$SO$_4$ and the solvent was evaporated to give 1.8 g (84%) of a yellow solid. H$^1$-NMR (400 MHz, CDCl$_3$): δ ppm 1.40 (s, 9H), 2.47 (s, 3H), 7.98, (s, 1H), 8.12 (s, 1H). LCMS: [Purosphoer@ star rp-18 (4.6×30) mm, 3 p.m. Mobile phase-A: 20 mm of ammonium acetate-90% of water-10% acetonitrile. Mobile phase-B: 20 mm of ammonium acetate in 10% of water-90% of acetonitrile. Flow rate: 2.5 ml/min] 95.6% (m/z=268.2). HPLC: [Sunfire C18, (150×4.6 mm) 3.5 µm, SC/862, Buffer: 0.5% TFA, in water pH adjusted to 2.5 using dil. Ammonia. Mobile phase-A: Buffer:acetonitrile (95:5), Mobile phase-B: acetonitrile:Buffer (95:5), Flow rate: 1 mL/min]: Purity- 96.68%

Step 6

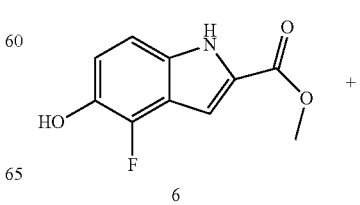

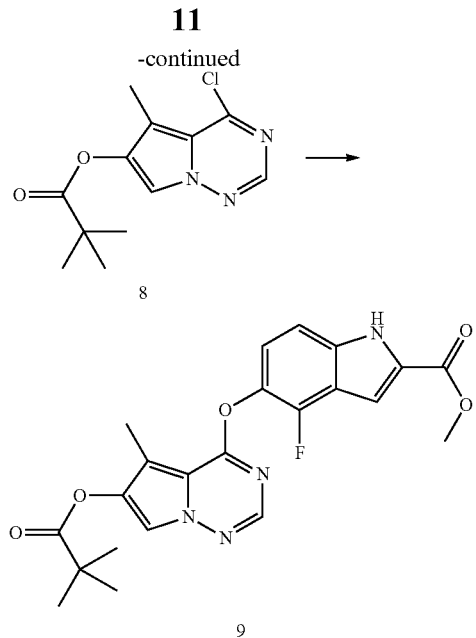

Indole derivative 6 (0.150 g, 0.7 mmol) was dissolved in DMF and then potassium carbonate (0.2980 g, 2.1 mmol) was added at 25° C., and stirred for 10 min. Pyrrolotriazine 8 (0.192 g, 0.7 mmol) was added and stirred for an additional 16 hr at room temperature. The reaction mixture was quenched with water and extracted into ethyl acetate. The organic layer was dried over $Na_2SO_4$ and concentrated to give 140 mg of crude compound which upon purification by column chromatography gave 70 mg (22%) of an off white compound. $H^1$-NMR (400 MHz, DMSO-$d_6$) δ ppm: 1.35 (s, 9H), 2.51 (s, 3H), 3.92 (s, 3H), 7.25 (d, J=2.0 Hz, 1H), 7.36 (d, J=J=2.8 Hz, 2H), 8.06 (s, 1H), 8.11 (s, 1H), 12.44 (s, 1H). LCMS: [Ascentis express C18, (5×2.1 mm) 2.7 μm, Mobile Phase-A: 2% acetonitrile-98% water with 10 mm of ammonium formate. Mobile phase-B: 98% acetonitrile:2% water with 10 mm of ammonium formate, Flow rate: 1 mL/min]: 85% (m/z=441.2).

Step 7:

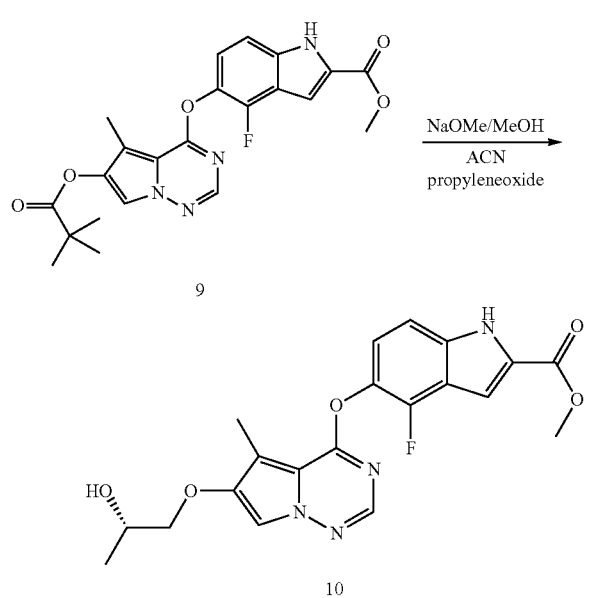

Compound 9 (100 mg, 0.22 mmol) was dissolved in acetonitrile (1 mL) under nitrogen atmosphere and cooled to 0° C.

25% of methanolic sodium methoxide (0.5 mL) was added dropwise and stirred an additional 8 hr. Water (1 mL) was added followed by propylene oxide (135 mg, 10 eq, 2.2 mmol) and stirring continued for 24 hr. Acetonitrile and methanol were removed under reduced pressure, and the reaction mixture was diluted with water, acidified to pH=3.0 with sulphuric acid (1.5 N, 0.5 mL) and extracted into ethyl acetate. The organic layer was dried over $Na_2SO_4$ and concentrated to afford 120 mg of crude solid. This was triturated with ethyl acetate:pet. ether (25% mixture) to afford 75 mg (80%) of purified compound as a green solid. $H^1$-NMR (400 MHz, $CDCl_3$) δ ppm: 0.85 (t, J=6.8, 2.2 Hz, 3H), 2.51 (d, J=8.8 Hz, 3H), 3.85 (q, J=7.5 1.6 Hz, 1H), 3.98 (s, 3H), 3.99 (s, 2H), 4.25 (bs, 1H), 7.24 (t, J=2.4, 4.8 Hz, 2H), 7.33 (d, J=2.0 Hz, 1H), 7.43 (s, 1H), 7.84 (s, 1H), 8.99 (bs, 1H). LCMS: [YMC pack TMS (50×3 mm) and 3 nm. Mobile phase-A: 2% acetonitrile-98% water with 10 mm ammonium formate. Mobile phase-B: 98% acetonitrile:2% water with 10 mm of ammonium formate. Flow rate: 1 mL/min]: 90.7% (m/z=415.2)

Step 8:

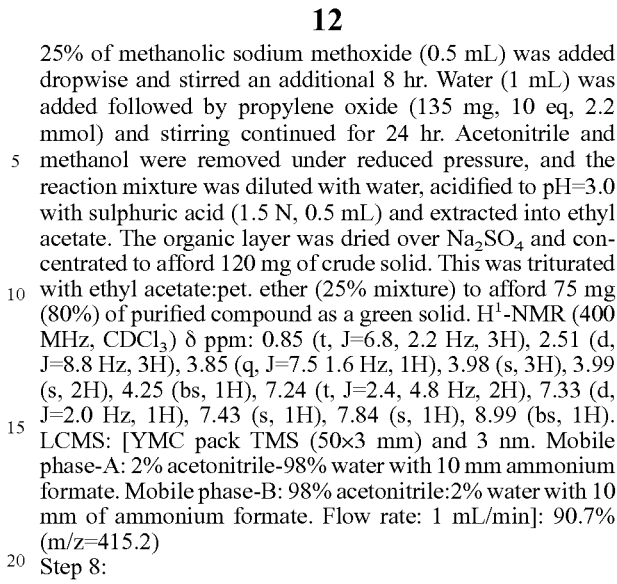

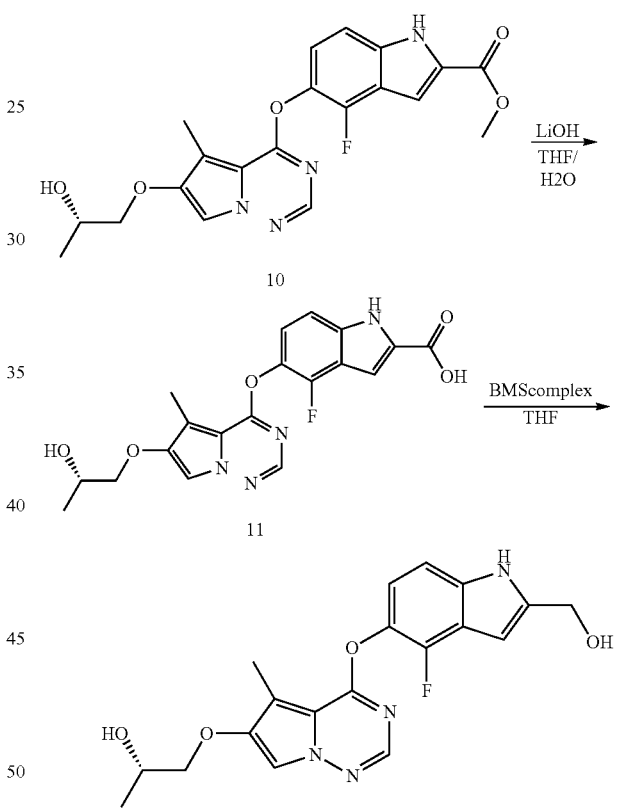

Compound 10 (0.140 g, 0.338 mmol) was dissolved in THF/water (3:1), lithium hydroxide was added and stirred for 5 hr. The reaction was monitored by TLC. After completion, the mixture was quenched with water; the pH was adjusted to 3 with dilute HCl and then extracted into ethyl acetate. The organic layer was washed with brine and dried over $Na_2SO_4$ and concentrated to give 0.1 g (74%) of an off-white solid. $H^1$-NMR (400 MHz, DMSO-$d_6$) δ ppm: 1.19 (d, J=6.0 Hz, 3H), 2.51 (s, 3H), 3.84-3.91 (m, 2H), 3.92-4.01 (m 1H), 7.05 (s, 1H), 7.24 (d, J=4.8 Hz, 1H), 7.29 (d, J=6.4 Hz, 1H), 7.91 (d, J=8 Hz, 2H), 12.05 (s, 1H). $C^{13}$-NMR (400 MHz, DMSO-$d_6$) δ ppm: 8.83, 8.95, 14.53, 17.09, 20.48, 60.21, 64.66, 64.99, 65.36, 76.88, 78.95, 100.60, 101.84, 102.76, 106.4, 107.58, 109.37, 110.58, 117.2, 117.39, 120.74, 130.61, 130.72, 131.74, 137.39, 137.48, 144.53, 144.67, 146.13, 147.68, 148.61, 148.72, 160.95, 162.92. LCMS: [Ascentis express C18, 5×2.1 mm) 2.7 nm, Mobile Phase-A: 2% acetonitrile-98% water with 10 mm of ammonium formate. Mobile phase-B: 98% acetonitrile: 2% water with 10 mm of ammonium formate, Flow rate: 1 mL/min]: 100% [m/z −399 (negative)]. HPLC: [Sunfire C18, (150×4.6 mm) 3.5 nm, SC/862, Buffer: 0.5% TFA, in water pH adjusted to 2.5 using dil. Ammonia. Mobile phase-A: Buffer:acetonitrile (95:5), Mobile phase-B: acetonitrile:Buffer (95:5), Flow rate: 1 mL/min]: 95.7%. Chiral HPLC: OJ-H (250×4.6 mm) 5 nm. Mobile phase-A: 0.2% DEA in hexane (80%) and B: Ethanol (20%); Flow rate: 1 mL/min.: 100%. Specific rotation: $[\alpha]_d$: −5.217 [c=0.115 temp: 23.7° C. in methanol).

Compound-11 (0.250 g, 0.625 mmol) was dissolved in THF (10 vol) under nitrogen atmosphere and cooled to 0° C. Borane-dimethyl sulphide complex (0.240 g, 3.125 mmol) was added slowly. The reaction mixture stirred for 3 hr at 45° C. After completion, the reaction mixture was quenched with methanol, and the solvent was evaporated off. The residue was diluted with water-ethyl acetate and the organic layer was separated. The separated organic layer was washed with brine and concentrated to give crude compound. The crude was subjected to prep-HPLC to afford 0.120 g of an off-white solid. $H^1$-NMR (400 MHz, DMSO) δ ppm: 1.18 (d, J=6.0 Hz, 3H), 2.51 (s, 3H), 3.80-3.91 (m, 2H), 3.99-4.02 (m, 1H), 4.63 (d, J=5.6 Hz, 2H), 4.89 (d, 4.4 Hz, 1H), 5.35 (t, J=5.6, 5.6 Hz, 1H), 6.39 (s, 1H), 7.04 (t, J=7.6, 8.4 Hz, 1H), 7.20 (d, J=8.4 Hz, 1H), 7.90 (d, J=7.2 Hz, 2H), 11.46 (s, 1H). LCMS: Ascentis express C18, 5×2.1 mm) 2.7 μm, Mobile Phase-A: 2% acetonitrile-98% water with 10 mm of ammonium formate. Mobile phase-B: 98% acetonitrile: 2% water with 10 mm of ammonium formate, Flow rate: 1 mL/min]: 98% (m/z=387.2). HPLC: [Sunfire C18, (150×4.6 mm) 3.5 μm, SC/862, Buffer: 0.5% TFA, in water pH adjusted to 2.5 using dil. Ammonia. Mobile phase-A: Buffer: acetonitrile (95:5), Mobile phase-B: acetonitrile:Buffer (95:5), Flow rate: 1 mL/min: Purity: 97.3% Chiral HPLC: OJ-H (250×4.6 mm) 5 μm. Mobile phase-A: 0.2% DEA in hexane (80%) and B: Ethanol (20%); Flow rate: 1 mL/min]: 91.92%. Specific rotation: $[\alpha]_d$: −3.00 [c=0.1 temp: 23.6° C. in methanol).

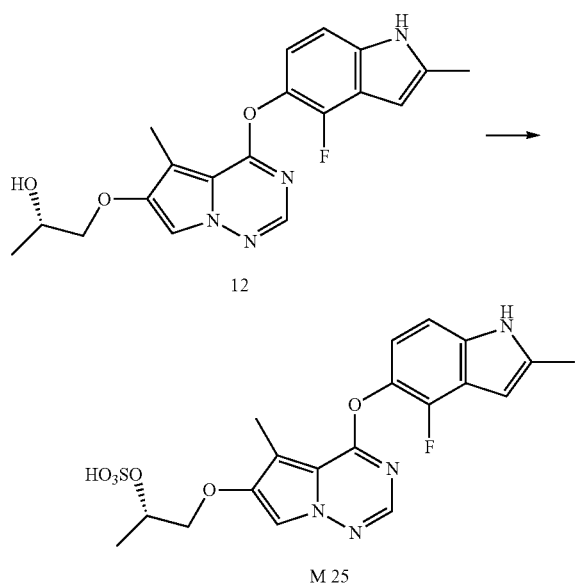

Compound 12 (0.5 g, 1.35 mmol) was dissolved in DMF (2 ml). Triethylamine-sulphur trioxide complex was added and stirring continued for 1 hr at room temperature. After completion, the reaction mixture was quenched with a solution of ammonium acetate in methanol and stirred an additional 10 minutes. The solvents were evaporated under vacuum. The residue obtained was slurried with 10% methanol in DCM and filtered. The obtained solid was washed many times with 10% methanol in DCM. The filtrate was concentrated to afford 0.25 g (41%). $H^1$-NMR (400 MHz, $CDCl_3$) δ ppm: 1.18 (t, J=3.2, 7.6 Hz, 3H), 3.07 (s, 6H), 4.01 (q, J=3.8, 4.4 Hz, 1H), 4.11 (dd, J=4.0, 4.0 Hz, 1H), 4.49-4.53 (m, 1H), 6.25 (s, 1H), 6.98 (s, 1H), 7.01 (dd, J=3.6, 3.6 Hz, 1H), 7.92 (s, 2H), 11.34 (s, 1H), $C^{13}$-NMR (400 MHz, $CDCl_3$) δ ppm: 8.76, 20.13, 56.88, 64.97, 76.69, 79.37, 94.97, 100.73, 106.18, 107.88, 110.63, 116.74, 130.24, 142.38, 144.56, 145.48, 148.62, 154.49, 161.27. LCMS: Zorbax SB C18 (4.6×50) mm, 5 μm, positive mode. Mobile phase-A: 10% methanol-90% water-0.1% TFA; Mobile phase-B: 90% Methanol-10% water-0.1% TFA. Flow rate: 5 mL/min: 98.94% (m/z: 451+ ve). HPLC: X Bridge, (150×4.6 mm) 3.5 μm: SC/840: Mobile Phase-A: 10 mm ammoniu bicarbonate in water pH=9.5 adjusted using dil ammonia. Mobile Phase b: methanol. Flow rate: 1 mL/min.: 99.2% s

Use and Utility

The compounds of the invention are useful for inhibiting protein kinases, such as, for example, VEGF. More specifically, the compounds inhibit the effects of VEGF, a property of value in the treatment of disease states associated with angiogenesis and/or increased vascular permeability such as cancer. The present invention also relates to a pharmaceutical composition comprising the compounds of the invention, and a pharmaceutically acceptable carrier or diluent; and to the use of this pharmaceutical composition in the treatment of hyperproliferative disorder in mammal In particular, the pharmaceutical composition may be employed to inhibit the growth of those primary and recurrent solid tumors which are associated with VEGF, especially those tumors which are significantly dependent on VEGF for their growth and spread, including for example, cancers of the bladder, squamous cell, head, colorectal, oesophageal, gynecological (such as ovarian), pancreas, breast, prostate, lung, vulva, skin, brain, genitourinary tract, non-small cell lung cancer (NSCLC), lymphatic system (such as thyroid), stomach, larynx, and lung. In another embodiment, the compounds of the invention are also useful in the treatment of noncancerous disorders such as diabetes, diabetic retinopathy, psoriasis, rheumatoid arthritis, obesity, Kaposi's sarcoma, haemangioma, acute and chronic nephropathies (including proliferative glomerulonephritis and diabetes-induced renal disease), atheroma, arterial restenosis, autoimmune diseases, acute inflammation and ocular diseases with retinal vessel proliferation, diabetic retinopathy, retinopathy of prematurity and macular degeneration. The compounds of the invention may be employed in the prevention of blastocyte implantation in a mammal, or in the treatment of atherosclerosis, eczema, scleroderma, or hemangioma. The compounds of the invention possess good activity against VEGF receptor tyrosine kinase while possessing some activity against other tyrosine kinases.

Thus according to a further aspect of the invention, there is provided the use of the compounds of the invention, in the manufacture of a medicament for use in the production of an antiangiogenic and/or vascular permeability reducing effect in a mammalian animal such as a human being.

According to a further feature of the invention there is provided a method for producing an antiangiogenic and/or vascular permeability reducing effect in a mammalian animal, such as a human being, in need of such treatment which comprises administering to said animal an effective amount of the compounds of the invention as defined herein before.

The compounds of the invention may also inhibit other receptor tyrosine kinases including HER1 and HER2 and is therefore useful in the treatment of proliferative disorders such as psoriasis and cancer. The HER1 receptor kinase has been shown to be expressed and activated in many solid tumors including non-small cell lung, colorectal, and breast cancer. Similarly, the HER2 receptor kinase has been shown to be overexpressed in breast, ovarian, lung, and gastric cancer. Monoclonal antibodies that downregulate the abundance of the HER2 receptor or inhibit signaling by the HER1 receptor have shown anti-tumor efficacy in preclinical and clinical studies. It is therefore expected that inhibitors of the HER1 and/or HER2 kinases will have efficacy in the treatment of tumors that depend on signaling from either of the two receptors. The ability of the compounds of the invention to inhibit HER1 further adds to their use as anti-angiogenic agents.

The antiproliferative, antiangiogenic, and/or vascular permeability reducing treatment defined herein before may be applied as a sole therapy or may involve, in addition to the compounds of the invention, one or more other substances and/or treatments. Such conjoint treatment may be achieved by way of the simultaneous, sequential, or separate administration of the individual components of the treatment. The compounds of the invention may also be useful in combination with known anti-cancer and cytotoxic agents and treatments, including radiation. If formulated as a fixed dose, such combination products employ the compounds of the invention within the dosage range described below and the other pharmaceutically active agent within its approved dosage range. The compounds of the invention may be used sequentially with known anticancer or cytotoxic agents and treatment, including radiation when a combination formulation is inappropriate.

In the field of medical oncology it is normal practice to use a combination of different forms of treatment to treat each patient with cancer. In medical oncology, the other component(s) of such conjoint treatment in addition to the antiproliferative, antiangiogenic, and/or vascular permeability reducing treatment defined herein before may be: surgery, radiotherapy, or chemotherapy. Such chemotherapy may cover three main categories of therapeutic agent:

(i) antiangiogenic agents that work by different mechanisms from those defined hereinbefore (for example, linomide, inhibitors of integrin $\alpha v \beta 3$ function, angiostatin, and razoxane);

(ii) cytostatic agents such as antiestrogens (for example tamoxifen, toremifene, raloxifene, droloxifene, and iodoxifene), progestogens (for example megestrol acetate), aromatase inhibitors (for example anastrozole, letrozole, borazole, and exemestane), antihormones, antiprogestogens, antiandrogens (for example flutamide, nilutamide, bicalutamide, and cyproterone acetate), LHRH agonists and antagonists (for example gosereline acetate and leuprolide), inhibitors of testosterone $5\alpha$-dihydroreductase (for example finasteride), farnesyltransferase inhibitors, anti-invasion agents (for example metalloproteinase inhibitors like marimastat and inhibitors of urokinase plasminogen activator receptor function) and inhibitors of growth factor function, (such growth factors include for example EGF, FGF, platelet derived growth factor and hepatocyte growth factor such as growth factor antibodies, growth factor receptor antibodies such as Avastin® (bevacizumab) and Erbitux® (cetuximab); tyrosine kinase inhibitors, and serine/threonine kinase inhibitors); and (iii) antiproliferative/antineoplastic drugs and combinations thereof, as used in medical oncology, such as antimetabolites (for example antifolates like methotrexate, fluoropyrimidines like 5-fluorouracil, purine and adenosine analogues, cytosine arabinoside); intercalating antitumor antibiotics (for example anthracyclines like doxorubicin, daunomycin, epirubicin, idarubicin, mitomycin-C, dactinomycin, and mithramycin); platinum derivatives (for example cisplatin and carboplatin); alkylating agents (for example nitrogen mustard, melphalan, chlorambucil, busulphan, cyclophosphamide, ifosfamide nitrosoureas, thiotepa; antimitotic agents (for example vinca alkaloids like vincristine and taxoids like Taxol® (paclitaxel), Taxotere® (docetaxel) and newer microbtubule agents such as epothilone analogs, discodermolide analogs, and eleutherobin analogs); topoisomerase inhibitors (for example epipodophyllotoxins like etoposide, teniposide, amsacrine, and topotecan); cell cycle inhibitors (for example flavopyridols); biological response modifiers, and proteasome inhibitors such as Velcade® (bortezomib).

As stated above, the compounds of the invention are of interest for their antiangiogenic and/or vascular permeability reducing effects. The compounds are expected to be useful in a wide range of disease states including cancer, diabetes, psoriasis, rheumatoid arthritis, Kaposi's sarcoma, haemangioma, obesity, acute and chronic nephropathies, atheroma, arterial restenosis, autoimmune diseases, acute inflammation and ocular diseases associated with retinal vessel proliferation such as diabetic retinopathy.

More specifically, the compounds of the invention are useful in the treatment of a variety of cancers, including (but not limited to) the following:

carcinoma, including that of the bladder, breast, colon, kidney, liver, lung, including small cell lung cancer, esophagus, gall bladder, ovary, pancreas, stomach, cervix, thyroid, prostate, and skin, including squamous cell carcinoma;

hematopoietic tumors of lymphoid lineage, including leukemia, acute lymphocytic leukemia, acute lymphoblastic leukemia, B-cell lymphoma, T-cell lymphoma, Hodgkins lymphoma, non-Hodgkins lymphoma, hairy cell lymphoma, and Burkett's lymphoma;

hematopoietic tumors of myeloid lineage, including acute and chronic myelogenous leukemias, myelodysplastic syndrome, and promyelocytic leukemia;

tumors of mesenchymal origin, including fibrosarcoma and rhabdomyosarcoma;

tumors of the central and peripheral nervous system, including astrocytoma, neuroblastoma, glioma, and schwannomas; and other tumors, including melanoma, seminoma, teratocarcinoma, osteosarcoma, xeroderma pigmentosum, keratoacanthoma, thyroid follicular cancer, and Kaposi's sarcoma.

Due to the key role of kinases in the regulation of cellular proliferation in general, inhibitors can act as reversible cytostatic agents which may be useful in the treatment of any disease process which features abnormal cellular proliferation, e.g., benign prostate hyperplasia, familial adenomatosis polyposis, neuro-fibromatosis, atherosclerosis, pulmonary fibrosis, arthritis, psoriasis, glomerulonephritis, restenosis following angioplasty or vascular surgery, hypertrophic scar formation, inflammatory bowel disease, transplantation rejection, endotoxic shock, and fungal infections.

The compounds of the invention are may induce or inhibit apoptosis. The apoptotic response is aberrant in a variety of human diseases. The compounds of the invention are, as modulators of apoptosis, would be useful in the treatment of cancer (including but not limited to those types mentioned hereinabove), viral infections (including but not limited to herpesvirus, poxvirus, Epstein-Barr virus, Sindbis virus and adenovirus), prevention of AIDS development in HIV-infected individuals, autoimmune diseases (including but not limited to systemic lupus, erythematosus, autoimmune mediated glomerulonephritis, rheumatoid arthritis, psoriasis, inflammatory bowel disease, and autoimmune diabetes mellitus), neurodegenerative disorders (including but not limited to Alzheimer's disease, AIDS-related dementia, Parkinson's disease, amyotrophic lateral sclerosis, retinitis pigmentosa, spinal muscular atrophy and cerebellar degeneration), myelodysplastic syndromes, aplastic anemia, ischemic injury associated with myocardial infarctions, stroke and reperfusion injury, arrhythmia, atherosclerosis, toxin-induced or alcohol related liver diseases, hematological diseases (including but not limited to chronic anemia and aplastic anemia), degenerative diseases of the musculoskeletal system (including but not limited to osteoporosis and arthritis) aspirin-sensitive rhinosinusitis, cystic fibrosis, multiple sclerosis, kidney diseases, and cancer pain.

The compounds of the invention are especially useful in treatment of tumors having a high incidence of tyrosine kinase activity, such as colon, lung, and pancreatic tumors. By the administration of a composition (or a combination) comprising the compounds of the invention, development of tumors in a mammalian host is reduced.

The compounds of the invention may also be useful in the treatment of diseases other than cancer that may be associated with signal transduction pathways operating through growth factor receptors such as VEGFR-2 and FGFR-1.

The phrase "radiation therapy" includes, but is not limited to, x-rays or gamma rays which are delivered from either an externally applied source such as a beam or by implantation of small radioactive sources. Radiation therapy may be useful in combination with the compounds of the present invention.

Another embodiment of the present invention is a pharmaceutical composition useful in the treatment of cancer, comprising the administration of a therapeutically effective amount of the compounds of the present invention, with or without pharmaceutically acceptable carriers or diluents. The compositions of the present invention may further comprise one or more pharmaceutically acceptable additional ingredient(s) such as alum, stabilizers, antimicrobial agents, buffers, coloring agents, flavoring agents, adjuvants, and the like. The compounds of the present invention and compositions of the present invention may be administered orally or parenterally including the intravenous, intramuscular, intraperitoneal, subcutaneous, rectal and topical routes of administration.

The pharmaceutical compositions may be administered by any means suitable for the condition to be treated, which may depend on the need for site-specific treatment or quantity of drug to be delivered. Topical administration is generally preferred for skin-related diseases, and systematic treatment preferred for cancerous or pre-cancerous conditions, although other modes of delivery are contemplated. For example, the compounds of the present invention may be delivered orally, such as in the form of tablets, capsules, granules, powders, or liquid formulations including syrups; topically, such as in the form of solutions, suspensions, gels or ointments; sublingually; bucally; parenterally, such as by subcutaneous, intravenous, intramuscular or intrasternal injection or infusion techniques (e.g., as sterile injectable aq. or non-aq. solutions or suspensions); nasally such as by inhalation spray; topically, such as in the form of a cream or ointment; rectally such as in the form of suppositories; or liposomally. Dosage unit formulations containing non-toxic, pharmaceutically acceptable vehicles or diluents may be administered. The compounds of the present invention, prepared according to the inventive process, may be administered in a form suitable for immediate release or extended release Immediate release or extended release may be achieved with suitable pharmaceutical compositions or, particularly in the case of extended release, with devices such as subcutaneous implants or osmotic pumps.

Exemplary compositions for parenteral administration include injectable solutions or suspensions which may contain, for example, suitable non-toxic, parenterally acceptable diluents or solvents, such as mannitol, 1,3-butanediol, water, Ringer's solution, an isotonic sodium chloride solution, or other suitable dispersing or wetting and suspending agents, including synthetic mono- or diglycerides, and fatty acids, including oleic acid.

Exemplary compositions for oral administration include suspensions comprising particles of the compounds dispersed in a liquid medium. The suspension may further comprise, for example, microcrystalline cellulose for imparting bulk, alginic acid or sodium alginate as a suspending agent, methylcellulose as a viscosity enhancer, and sweeteners or flavoring agents such as those known in the art; and immediate release tablets which may contain, for example, microcrystalline cellulose, dicalcium phosphate, starch, magnesium stearate, and/or lactose and/or other excipients, binders, extenders, disintegrants, diluents, and lubricants such as those known in the art. The compounds also may be delivered by sublingual and/or buccal administration, e.g. with molded, compressed, or freeze-dried tablets. Exemplary compositions may include fast-dissolving diluents such as mannitol, lactose, sucrose, and/or cyclodextrins. Also, included in such formulations may be high molecular weight excipients such as celluloses (AVICEL®) or polyethylene glycols (PEG); an excipient to aid mucosal adhesion such as hydroxypropyl cellulose (HPC), hydroxypropyl methyl cellulose (HPMC), sodium carboxymethyl cellulose (SCMC), and/or maleic anhydride copolymer (e.g., GANTREZ®); and agents to control release such as polyacrylic copolymer (CARBOPOL 934®). Lubricants, glidants, flavors, coloring agents, and stabilizers may also be added for ease of fabrication and use.

An example of a composition for oral administration is one or more of the compounds, lactose monohydrate (intra-granular phase), microcrystalline cellulose (intra-granular phase), croscarmellose sodium (intra-granular phase), hydroxypropyl cellulose (intra-granular phase), microcrystalline cellulose (extra-granular phase), croscarmellose sodium (extra-granular phase), and magnesium stearate (extragranular phase).

The effective amount of the compounds may be determined by one of ordinary skill in the art, and includes exemplary dosage amounts for a mammal of from about 0.05 to about 300 mg/kg/day, preferably less than about 200 mg/kg/day, in a single dose or in 2 to 4 divided doses. It will be understood that the specific dose level and frequency of dosage for any particular subject may be varied and will depend upon a variety of factors, the bioavailability of the compounds, the metabolic stability and length of action of the compounds, the species, age, body weight, general health, sex, and diet of the subject, the mode and time of administration, rate of excretion, drug combination, and severity of the particular condition. Preferred subjects for treatment include animals, most preferably mammalian species such as humans and domestic animals such as dogs, cats, horses, and the like.

Typically, the solid form of a pharmaceutically active material is important in the preparation of a solid dosage form, such as tablets or capsules as the manufacturing, stability, and/or the performance of the pharmaceutically active material can be dependent upon the solid form.

Kinase Assay

KDR (h) Kinase

The biochemical kinase assay to quantitate the inhibition of kinase activity by test compounds was performed in vitro in 96-well plates. All test compounds were dissolved in 100% DMSO and diluted into 2× the final concentration with PBS/ 1% DMSO prior to assay. The incubation mixture consisted of 20 mM MOPS, 1 mM EDTA, 0.01% Brij-35, 5% Glycerol, 0.1% β-mercaptoethanol and 1 mg/mL BSA. The reaction was initiated by the addition of the MgATP mix. After incubation for 40 minutes at room temperature, the reaction was stopped by the addition of 3% phosphoric acid solution. 10 μL of the reaction was then spotted onto a P30 filtermat and washed three times for 5 minutes in 75 mM phosphoric acid and once in methanol prior to drying and scintillation counting. Dose-response curses were generated to determine the concentration of the inhibitors required to inhibit 50% of kinase activity ($IC_{50}$). $IC_{50}$ values were derived by non-linear regression analysis. The reported $IC_{50}$ value was the average of at least three separate experiments.

All of the compounds of the invention exhibited activity in this assay.

What is claimed is:

1. A substantially pure compound which is a metabolite of the compound of formula (I)

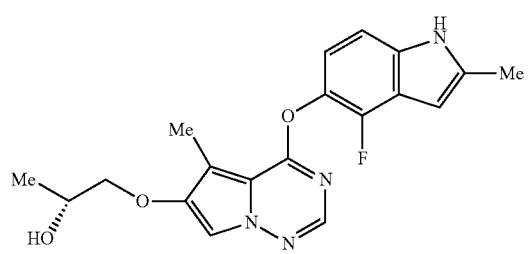

(I)

or a pharmaceutically acceptable salt form thereof, which metabolite is

1)

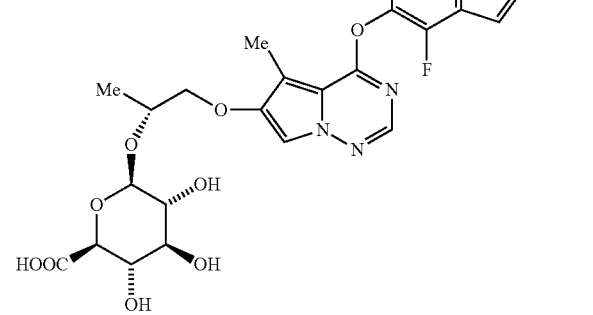

(II)

or a pharmaceutically acceptable salt form thereof, or which metabolite is

2)

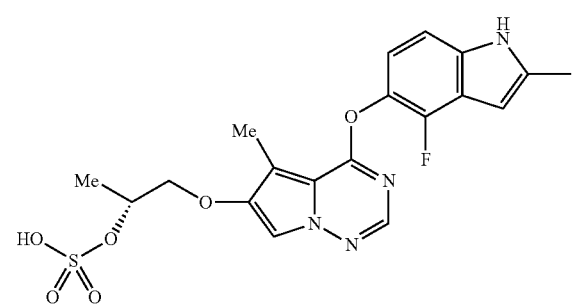

(III)

or a pharmaceutically acceptable salt form thereof, or which metabolite is

3)

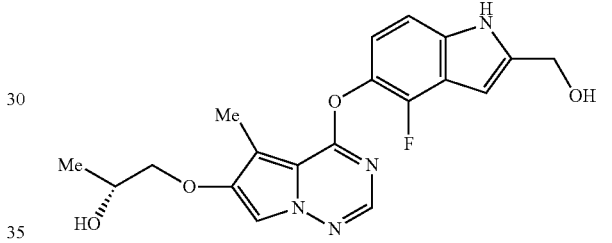

(IV)

or a pharmaceutically acceptable salt form thereof.

2. A pharmaceutical composition, comprising a pharmaceutically acceptable vehicle or diluent and one or more compounds of claim 1.

3. A method of treating cancer, comprising the step of administering to a subject in need thereof an effective amount of the compound of claim 1, wherein the cancer is selected from breast cancer, colorectal cancer, hepatocellular carcinoma, non-small cell lung cancer and prostate cancer.

4. The compound according to claim 1 which is

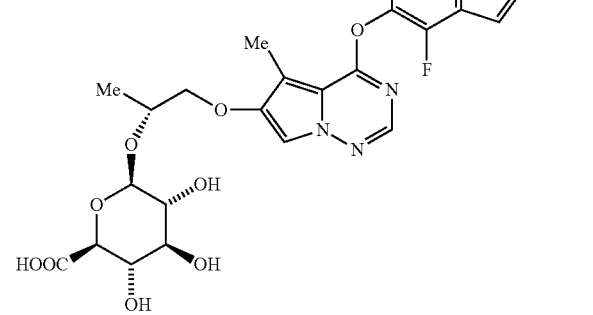

(II)

or a pharmaceutically acceptable salt form thereof.

5. The compound according to claim 1 which is

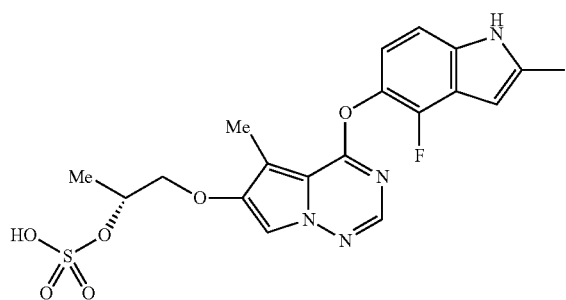

(III)

or a pharmaceutically acceptable salt form thereof.

6. The compound according to claim 1 which is

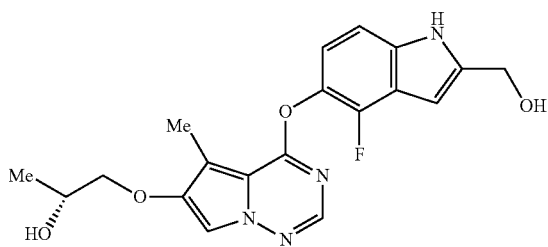

(IV)

or a pharmaceutically acceptable salt form thereof.

7. A pharmaceutical composition, comprising a pharmaceutically acceptable vehicle or diluent and the compound of claim 4.

8. A method of treating cancer, comprising the step of administering to a subject in need thereof an effective amount of the compound of claim 4, wherein the cancer is selected from breast cancer, colorectal cancer, hepatocellular carcinoma, non-small cell lung cancer and prostate cancer.

9. A pharmaceutical composition, comprising a pharmaceutically acceptable vehicle or diluent and the compound of claim 5.

10. A method of treating cancer, comprising the step of administering to a subject in need thereof an effective amount of the compound of claim 5, wherein the cancer is selected from breast cancer, colorectal cancer, hepatocellular carcinoma, non-small cell lung cancer and prostate cancer.

11. A pharmaceutical composition, comprising a pharmaceutically acceptable vehicle or diluent and the compound of claim 6.

12. A method of treating cancer, comprising the step of administering to a subject in need thereof an effective amount of the compound of claim 6, wherein the cancer is selected from breast cancer, colorectal cancer, hepatocellular carcinoma, non-small cell lung cancer and prostate cancer.

* * * * *